(12) United States Patent
Mathieu et al.

(10) Patent No.: US 12,356,968 B2
(45) Date of Patent: Jul. 15, 2025

(54) EGG-LAYING MEDIUM FOR INSECTS COMPRISING A SOLID SUBSTRATE

(71) Applicant: YNSECT, Evry Courcouronnes (FR)

(72) Inventors: Marianne Mathieu, Saint Pierre les Nemours (FR); Pedro Escalante Noguera, Juvisy sur Orge (FR); Fabrice Berro, Paris (FR); Thibault Du Jonchay, Chevrières (FR); Nathalie Berezina, Järfälla (SE)

(73) Assignee: YNSECT, Evry Courcouronnes (FR)

( * ) Notice: Subject to any disclaimer, the term of this patent is extended or adjusted under 35 U.S.C. 154(b) by 412 days.

(21) Appl. No.: 17/059,784

(22) PCT Filed: May 31, 2019

(86) PCT No.: PCT/FR2019/051285
§ 371 (c)(1),
(2) Date: Nov. 30, 2020

(87) PCT Pub. No.: WO2019/229397
PCT Pub. Date: Dec. 5, 2019

(65) Prior Publication Data
US 2021/0204532 A1  Jul. 8, 2021

(30) Foreign Application Priority Data
Jun. 1, 2018  (FR) ..................... 1854800

(51) Int. Cl.
*A01K 67/30* (2025.01)
(52) U.S. Cl.
CPC ........ *A01K 67/30* (2025.01); *A01K 2227/706* (2013.01)

(58) Field of Classification Search
CPC ................ A01K 67/033; A01K 2227/706
See application file for complete search history.

(56) References Cited

U.S. PATENT DOCUMENTS

| | | | |
|---|---|---|---|
| 7,789,039 B2 * | 9/2010 | Hance | A01N 25/26 119/6.5 |
| 8,647,686 B1 * | 2/2014 | Rojas | A23K 20/20 426/74 |

(Continued)

FOREIGN PATENT DOCUMENTS

| | | |
|---|---|---|
| FR | 2835701 | 8/2003 |
| WO | WO 2014/046529 | 3/2014 |

OTHER PUBLICATIONS

Brightsmith, retrieved from https://vetmed.tamu.edu/news/press-releases/texas-am-professor-explores-why-peruvian-parrots-eat-clay/ (Year: 2017).*

(Continued)

*Primary Examiner* — Joshua J Michener
*Assistant Examiner* — Aaron M Rodziwicz
(74) *Attorney, Agent, or Firm* — Panitch Schwarze Belisario & Nadel LLP; Erin M. Dunston; Christopher L. North

(57) ABSTRACT

Breeding of insects and the separation of insect eggs from other constituents of an egg-laying medium. An egg-laying medium for insects, comprising at least 80% by weight of a solid substrate in the form of particles, at least 85% by weight of said particles having a size of less than 0.5 mm, wherein the weight percentage is given in relation to the total weight of the insect egg-laying medium. Also a laying tray and uses thereof, particularly in a method for collecting insect eggs.

17 Claims, 3 Drawing Sheets

(56) References Cited

U.S. PATENT DOCUMENTS

| | | | |
|---|---|---|---|
| 10,405,528 B2* | 9/2019 | Comparat | B65G 1/0407 |
| 10,842,138 B1* | 11/2020 | Lolley | A01K 67/033 |
| 2004/0228947 A1* | 11/2004 | Wiggins | A01K 67/033 |
| | | | 426/2 |
| 2009/0000553 A1 | 1/2009 | Ramos Elorduy Y Blasquez | |
| 2017/0202191 A1* | 7/2017 | Marchant | F21V 7/22 |
| 2017/0325431 A1* | 11/2017 | Leo | A23K 20/174 |
| 2018/0007874 A1* | 1/2018 | Hall | A01K 7/02 |
| 2018/0103679 A1* | 4/2018 | Leo | A01K 67/033 |
| 2021/0137137 A1* | 5/2021 | Leo | B01D 3/145 |

OTHER PUBLICATIONS

Fao, *texture du sol*, http://blog.ac-versailles.fr/formation/capa/public/le_sol/LE_SOL_2_.pdf (Jul. 31, 2013).

House, *An Artificial Host: Encapsulated Synthetic Medium for In Vitro Oviposition and Rearing the Endoparasitoid Itoplectis Conquisitor (Hymenoptera: Ichneumonidae)*, 110(3) The Canadian Entomologist 331-333 (Mar. 1, 1978).

Food and Agriculture Organization of the United Nations, Simple Methods for Aquaculture, Soil, 6. Soil Texture. CD-ROM (available at www.fao.org/fishery/static/FAO_Training/FAO_Training/General/x6706e/x6706e06.htm) (2006).

* cited by examiner

EGG-LAYING MEDIUM FOR INSECTS COMPRISING A SOLID SUBSTRATE

CROSS-REFERENCE TO RELATED APPLICATIONS

This application is a U.S. National Stage Application pursuant to 35 U.S.C. § 371 of International Patent Application PCT/FR2019/051285, filed on May 31, 2019, and published as WO 2019/229397 on Dec. 5, 2019, which claims priority to French Patent Application 1854800, filed on Jun. 1, 2018, all of which are incorporated herein by reference in their entireties for all purposes.

BACKGROUND OF THE INVENTION

The present invention relates to the breeding of insects and more particularly the breeding of coleopterans and/or lepidopterans. It relates more particularly to an egg-laying medium and a laying tray, and the uses thereof, in particular in a method for collecting insect eggs.

The breeding of insects has experienced significant growth over the last few years. The production of insects has numerous benefits, whether for agro-industries, as insects constitute a good source of proteins, or in other industrial fields, as insects are also a source of chitin, which can be converted to chitosan, which has numerous applications: cosmetic, medical and pharmaceutical, dietary and food, water treatment, etc.

The breeding of insects on an industrial scale assumes that the insects can be made to reproduce efficiently.

Most often, during breeding, the female insects lay eggs in their nutrient medium. These eggs, which are often very small, hatch a few weeks after laying. Sometimes, the larvae which have just hatched devour the eggs that have not hatched yet. Hence the necessity of separating the eggs from the larval population in order to maintain a high level of production.

However, there is therefore a need for a method for collecting eggs which is efficient on an industrial scale.

KR20130046658 relates to a method for gathering eggs of a *Tenebrio molitor* (or *T. molitor*) insect, comprising a container and a removable filtering net, the method comprising in particular the following steps: introducing cereal flour into a container, introducing individuals at the adult stage into the removable filtering net, making the females lay eggs in such a way that the eggs are stuck to the wall of the container, and recovering the eggs on the one hand and, by means of the removable filtering net, the females on the other hand.

However, this document does not clearly describe how the females are made to lay the eggs in such a way that the eggs are stuck to the wall of the container. Moreover, such a method is not suitable at industrial scale, which involves a high level of productivity, in particular in areal terms.

BRIEF SUMMARY OF THE INVENTION

The present invention aims to propose a method for collecting insect eggs which makes it possible to overcome the above drawbacks. By "insect eggs" is meant more particularly isolated insect eggs, i.e. which are not in the form of heaps, called egg sacs.

The inventors' work has allowed them to develop this collection method, which requires the use of a specific egg-laying medium.

DETAILED DESCRIPTION OF THE INVENTION

Figure 1:
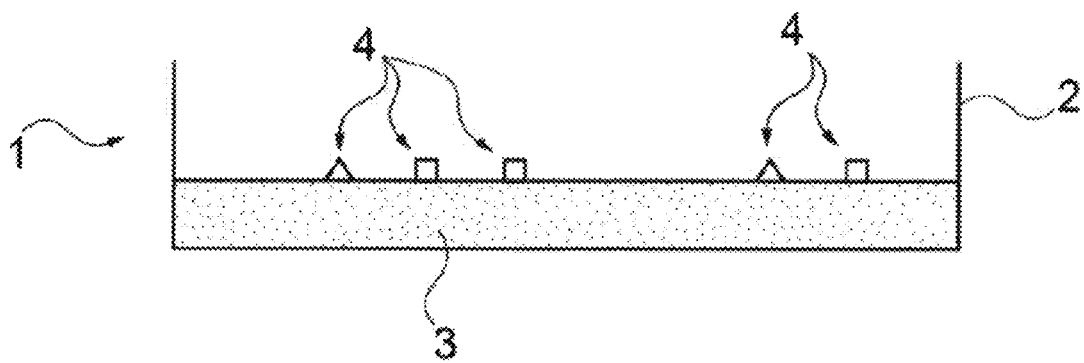
FIG. 1 is a diagram of a laying tray according to the invention.

The invention therefore relates to an egg-laying medium for insects, comprising:
  at least 80% by weight of a solid substrate in the form of particles, at least 85% by weight of said particles having a particle size smaller than 0.5 mm, said solid substrate having a moisture content comprised between 0 and 15%,
  wherein the percentage by weight is given in relation to the total weight of egg-laying medium for insects.

It will be noted that, in the context of the present application, and unless otherwise stipulated, the ranges of values indicated are understood to be inclusive.

By "solid substrate" is meant a solid substrate or a mixture of solid substrates intended to be consumed by the insects.

Preferably, the egg-laying medium for insects comprises:
  from 90% to 98% by weight of a solid substrate in the form of particles, at least 85% by weight of said particles having a particle size smaller than 0.5 mm, and said solid substrate having a moisture content comprised between 0 and 15%,
wherein the percentage by weight is given in relation to the total weight of egg-laying medium for insects.

Particle size is a characteristic well known to a person skilled in the art, which makes it possible to characterize compositions such as, for example, powders, coarse meal.

By way of example, the solid substrate can in fact be in the form of a powder, a coarse meal.

Granulometry is the study of the size distribution of the particles in a composition. The techniques for granulometric analysis are well known to a person skilled in the art. By way of example, reference may be made to the following publication: "La granulométrie de l'aliment: principe, mesure et obtention" [Granulometry of food: principle, measurement and obtention]; INRA Prod. Anim., 2000, 13 (2), 81-97.

By "particles having a size smaller than Y" is meant particles which pass through a sieve having an aperture size of Y.

Preferably, at least 90% by weight of the particles of the solid substrate have a size smaller than 0.5 mm.

Preferably, the solid substrate has a moisture content comprised between 0 and 10%.

Preferably, the solid substrate is a solid product or co-product originating from the conversion of cereals, oilseeds, protein-oil crops and/or protein crops.

A co-product is an unavoidable substance created during a process of manufacturing a product of interest.

More particularly, the solid substrate is advantageously a product or co-product originating from the conversion of wheat (common wheat, durum wheat), maize, barley, rice, triticale, common oats, sorghum, rye, spelt, millet, *quinoa*, buckwheat, rapeseed, sunflower, flax, soya and/or pea.

Preferably, the solid substrate is a product or co-product originating from the conversion of wheat, more preferably the substrate is wheat bran and/or wheat feed.

Alternatively, dried distilled grains with solubles can be used.

As indicated above, the solid substrate must have a particle size smaller than 0.5 mm.

This particle size makes it possible easily and cleanly to separate the insect eggs from the other constituents of the egg-laying medium.

However, if the solid product or co-product originating from the conversion of the cereals, oilseeds, protein-oil crops and/or protein crops has a particle size larger than 0.5 mm, it can be subjected to a grinding step, so to obtain a solid substrate having a particle size smaller than 0.5 mm. This is the case for example for wheat bran, 75% by weight of wheat bran particles having a particle size larger than 0.8 and smaller than 1.4 mm.

This grinding step can be carried out with the aid of any suitable type of grinder. These grinders are well known to a person skilled in the art.

The solid substrate (or the mixture of solid substrates) has a moisture content comprised between 0 and 15%, preferably between 0 and 10%. Therefore, it is necessary to supply additional water. This supply of additional water can, for example, be effected via the addition of water in spray form, the introduction of aqueous vegetables, such as for example vegetables having at least 60% moisture content (carrots, potatoes, etc.) and/or via the introduction of an aqueous and optionally nutritional gel.

When an aqueous and optionally nutritional gel is used to supply water, it is introduced in a quantity of at least 2% by weight, in relation to the total weight of the egg-laying medium for insects.

The invention therefore relates more particularly to an egg-laying medium for insects, comprising:
- at least 80% by weight of a solid substrate in the form of particles, at least 85% by weight of said particles having a particle size smaller than 0.5 mm, said solid substrate having a moisture content comprised between 0 and 15%, and
- at least 2% by weight of an aqueous and optionally nutritional gel, wherein the percentages by weight are given in relation to the total weight of egg-laying medium for insects.

Preferably, the egg-laying medium for insects comprises:
95 to 97% of a solid substrate in the form of particles, at least 85% by weight of said particles having a particle size smaller than 0.5 mm, said solid substrate having a moisture content comprised between 0 and 15%, and
3% to 5% by weight of an aqueous and optionally nutritional gel, wherein the percentages by weight are given in relation to the total weight of egg-laying medium for insects.

Advantageously, the aqueous and optionally nutritional gel comprises:
at least 90% by weight of an aqueous solution,
0.3 to 2% by weight of a gelling agent, and
0.1 to 5% by weight of a preservative,
wherein the percentages by weight are expressed in relation to the total weight of the gel.

Preferably, the aqueous and optionally nutritional gel has a water content greater than 50%, preferably greater than 70%, still more preferably greater than 90% by weight relative to the total weight of gel.

According to a first embodiment of the aqueous and optionally nutritional gel, the aqueous solution is constituted by water.

According to a second embodiment of the aqueous and optionally nutritional gel, the gel is also nutritional and the aqueous solution can contain, besides water, a liquid agro-industry co-product. Preferably, the agro-industry is chosen from the industries of starch production, potato starch production, malting, bioethanol production, sugar production, fermentation, brewing, distillation and dairy. Preferably, the liquid agro-industry co-product is chosen from the list constituted by cereal solubles, maize solubles, wheat solubles, pea solubles, cassava solubles, sugar beet solubles, sugarcane solubles, cereal distillation solubles, wheat distillation solubles, maize distillation solubles, pea distillation solubles, cassava distillation solubles, vinasses, molasses, cream yeasts, wheys and concentrated derivatives thereof, in particular the permeate, or mixtures thereof. More preferably, the liquid agro-industry co-product is chosen from a distillation soluble or a mixture of a distillation soluble and another liquid co-product.

Advantageously, the gelling agent is chosen from the group constituted by xanthan gum, carob bean gum, guar gum, or a mixture thereof. Preferably, the gelling agent is a mixture of xanthan gum and carob bean gum or of xanthan gum and guar gum.

The aqueous and optionally nutritional gel can also contain yeasts, vitamins and/or probiotics.

Advantageously, the aqueous and optionally nutritional gel has a gel strength of at least 20 g/cm$^2$, preferably 30 g/cm$^2$, more preferably 50 g/cm$^2$.

This gel strength makes it possible to obtain a solid gel with a structure that is not very viscous, which will not be dried out by the presence of fine particles likely to adhere to the gel.

Preferably, the solid substrate has a particle size comprised between 0.3 and 0.5 mm, i.e. at least 50% of the particles have a size larger than 0.3 and smaller than 0.5 mm.

A substrate particle size comprised between 0.3 and 0.5 mm has the advantage in particular of preventing the aqueous gel from drying out.

By the choice of the different parameters set out above, the egg-laying medium for insects according to the invention makes it possible in particular:
- Easily and cleanly to separate the insect eggs from the other constituents of the egg-laying medium: adults, residues of dead adults, excrement (frass), substrates and possibly gel. This makes it possible in particular to increase production densities, obtaining a better productivity per unit of surface area;
- To solve the problems of the development of opportunistic parasites (mites, flies, etc.) which can colonize the nutrient substrates insufficiently consumed by the adults and small larvae. The presence of substrates not consumed over an extended period is mainly due to the difficulties of concentrating the insects from the egg stage to the 20 mg larva phase. This is also effected by controlling the moisture content;
- To increase the reproduction performance. This increase can be explained in particular by the choice of the egg-laying medium, which in particular promotes a decrease in the accidental consumption of the eggs by the adults. Usually, under denser conditions, the probability of such events occurring is higher. The choice of the egg-laying medium makes it possible to collect the eggs more easily, wherein the frequency of this collection can be increased, thus limiting this phenomenon;

While maintaining a high level of productivity.

The egg-laying medium according to the invention is advantageously arranged on the bottom of a container in order to form a laying tray.

The invention also relates to a laying tray comprising a container and, on a bottom of said container:
- 0.12 to 7.5 g/cm² of a solid substrate in the form of particles, at least 85% by weight of said particles having a particle size smaller than 0.5 mm, said solid substrate having a moisture content comprised between 0 and 15%.

The areal quantities are expressed in relation to the surface area of the bottom of the container. Such a laying tray is suitable for insects.

Preferably, the laying tray according to the invention moreover comprises, on the bottom of said container:
- 0.006 to 0.325 g/cm² or 0.0016 to 0.095 g/cm²/d of an aqueous and optionally nutritional gel.

It will be noted that the quantities in g/cm²/d are dependent on the residence time of the insects in days (d). Typically, the quantity in g/cm²/d indicated above corresponds to a residence of the insects of 7 d, during which residence the gel content will be replenished once.

Preferably, the surface of the bottom of the container of the laying tray comprises:
- 0.17 to 6.95 g/cm² of a solid substrate in the form of particles, at least 85% by weight of said particles having a particle size smaller than 0.5 mm, said solid substrate having a moisture content comprised between 0 and 15%, and
- 0.0074 to 0.275 g/cm² or 0.0022 to 0.08 g/cm²/d of an aqueous and optionally nutritional gel.

Preferably, in particular, in the laying tray:
- the solid substrate in the form of particles is present in a content of from 90% to 98% by weight, at least 85% by weight of said particles having a particle size smaller than 0.5 mm;
- at least 90% by weight of the particles of the solid substrate have a size smaller than 0.5 mm;
- the solid substrate has a moisture content comprised between 0 and 10%;
- the solid substrate is a solid product or co-product originating from the conversion of cereals and/or oilseeds/protein-oil crops which can have the particular, advantageous and preferred characteristics as indicated for the egg-laying medium above;
- the aqueous and optionally nutritional gel comprises:
  - at least 90% by weight of an aqueous solution,
  - 0.3 to 2% by weight of a gelling agent, and
  - 0.1 to 5% by weight of a preservative,
  wherein the percentages by weight are expressed in relation to the total weight of the gel; said aqueous and optionally nutritional gel being able to have the particular, advantageous and preferred characteristics as indicated for the egg-laying medium above; in particular, the aqueous and optionally nutritional gel has a water content greater than 50%, preferably greater than 70%, still more preferably greater than 90% by weight relative to the total weight of gel.

The invention also relates to the use of an egg-laying medium according to the invention, a laying tray according to the invention for breeding coleopterans and/or lepidopterans.

By coleopterans and/or lepidopterans is meant more particularly the coleopterans and lepidopterans belonging to the families of the Tenebrionidae, Melolonthidae, Dermestidae, Coccinellidae, Cerambycidae, Carabidae, Buprestidae, Cetoniidae, Dryophthoridae, Silvanidae, *Trogoderma*, Laemophloeidae, Trogossitidae, Pyralidae or mixtures thereof.

More preferably, they are the following coleopterans and/or lepidopterans: *Tenebrio molitor, Tenebrio obscurus, Tribolium castaneum, Tribolium confusum, Dermestes ater, Dermestes magister, Alphitobius diaperinus, Zophobas morio, Rhynchophorus ferrugineus, Oryzaephilus surinamensis, Cryptolestes ferrugineus, Trogoderma granarium, Gnathocerus cornutus, Tenebroides mauritanicus* and *Ephestia kuehniella*.

More preferably, the egg-laying medium according to the invention and the laying tray according to the invention are utilized in the breeding of coleopterans, in particular from the families of the Tenebrionidae, Melolonthidae, Dermestidae, Coccinellidae, Cerambycidae, Carabidae, Buprestidae, Cetoniidae and Dryophthoridae.

More preferably, they are the coleopterans *Tenebrio molitor, Tenebrio obscurus, Tribolium castaneum, Alphitobius diaperinus, Zophobas morio, Rhynchophorus ferrugineus*, or a mixture thereof, and more particularly in the breeding of *Tenebrio molitor*.

Finally, the invention relates to a method for obtaining insect eggs, comprising the steps of:
- obtaining a laying tray by providing a container and filling said container with:
  - a solid substrate in the form of particles, at least 85% by weight of said particles having a particle size smaller than 0.5 mm, said solid substrate having a moisture content comprised between 0 and 15%,
  in order to obtain a laying tray,
- introducing adult insects into the laying tray, and
- a subsequent step of collecting the insect eggs.

In the method for obtaining insect eggs according to the invention, the step of filling the container with the solid substrate is effected by supplying 0.12 to 7.5 g/cm² of said solid substrate into the container.

Preferably, the step of filling the container with the solid substrate is effected by supplying 0.17 to 6.95 g/cm² of solid substrate.

Advantageously, the supply of solid substrate into the container is effected to a height of from 1 to 5 cm, preferably to a height of from 2 to 4 cm.

Preferably, in the method for obtaining insect eggs according to the invention, the step of filling the container comprises introducing an aqueous and optionally nutritional gel in a supply of from 0.0016 to 0.095 g/cm²/d, more preferably in a supply of from 0.0022 to 0.08 g/cm²/d.

The quantity of aqueous and optionally nutritional gel in g/cm²/d is dependent on the residence time of the insects in the laying tray in days (d). This residence time corresponds to the number of days elapsed from the introduction of the insects into the laying tray and the step of collecting the eggs.

For a residence time of 3.5 days, the quantity of aqueous and optionally nutritional gel is from 0.006 to 0.325 g/cm², preferably from 0.0074 to 0.275 g/cm².

Advantageously, in the method for obtaining insect eggs according to the invention, the step of introducing the adult insects into the laying tray is effected in an areal density comprised between 0.01 and 1.0 g/cm², preferably in an areal density comprised between 0.02 and 0.75 g/cm².

Preferably, the method for obtaining insect eggs according to the invention comprises the following steps:
- obtaining a laying tray by providing a container and filling a bottom of said container with:
  - 0.17 to 6.95 g/cm² of a solid substrate in the form of particles, at least 85% by weight of said particles having a particle size smaller than 0.5 mm, said solid substrate having a moisture content comprised between 0 and 15%,
0.0022 to 0.08 g/cm²/d of an aqueous and optionally nutritional gel,
introducing adult insects into the laying tray, and
a subsequent step of collecting the insect eggs.

Alternatively, the method for obtaining insect eggs according to the invention comprises the following steps:
obtaining a laying tray by providing a container and filling a bottom of said container with:
0.17 to 6.95 g/cm² of a solid substrate in the form of particles, at least 85% by weight of said particles having a particle size smaller than 0.5 mm, said solid substrate having a moisture content comprised between 0 and 15%,
0.0074 to 0.275 g/cm² of an aqueous and optionally nutritional gel,
introducing adult insects into the laying tray, and
a subsequent step of collecting the insect eggs.

Such a method is suitable for a residence of the insects in the laying tray of 7 d, during which residence the gel content will be replenished once, for example during day 3, day 1 being the day on which the adult insects are introduced into the laying tray.

According to a particularly advantageous embodiment, the subsequent step of collecting the eggs in the method for obtaining insect eggs according to the invention is effected by means of an automated sorting step.

The automated sorting step makes it possible easily to separate the different elements contained in the laying tray.

This automated sorting step can be effected by means of devices such as tumbler screening machines or linear screening machines.

These devices make it possible easily to separate different fractions, classified hereafter by increasing size:
The solid substrate fraction,
The adult insect excrement fraction,
The insect egg fraction,
The dead adult insect residue fraction,
The adult insect fraction.

At the end of the automated sorting step, the recovery of the insect egg fraction makes it possible to collect the eggs.

As the egg fraction can comprise impurities, it is possible to effect an additional separation step in order to obtain pure and clean eggs. In this case, the egg fraction is subjected to a density separation with a rate of air-flow suitable for the quantity of eggs in order to make it possible to obtain pure and clean eggs.

Alternatively, it is possible to use the egg fraction as is.

Furthermore, the automated sorting also makes it possible to separate and collect the adult insects. The living adults can then be separated from the dead adults with the aid of a density column. Once separated, the living adult insects can be re-used in order to populate a new laying tray according to the invention.

Preferably, the collecting step in the method for obtaining insect eggs according to the invention is effected every 2 to 3 days.

A harvesting every 2 to 3 days makes it possible to increase the laying performance by at least 20%.

Preferably, in particular, in the method for obtaining insect eggs according to the invention:
the solid substrate in the form of particles is present in a content of from 90% to 98% by weight, at least 85% by weight of said particles having a particle size smaller than 0.5 mm;
at least 90% by weight of the particles of the solid substrate have a size smaller than 0.5 mm;
the solid substrate has a moisture content comprised between 0 and 10%;
the solid substrate is a solid product or co-product originating from the conversion of cereals and/or oilseeds/protein-oil crops which can have the particular, advantageous and preferred characteristics as indicated for the egg-laying medium above;
the aqueous and optionally nutritional gel comprises:
at least 90% by weight of an aqueous solution,
0.3 to 2% by weight of a gelling agent, and
0.1 to 5% by weight of a preservative,
wherein the percentages by weight are expressed in relation to the total weight of the gel; said aqueous and optionally nutritional gel being able to have the particular, advantageous and preferred characteristics as indicated for the egg-laying medium above; in particular, the aqueous and optionally nutritional gel has a water content greater than 50%, preferably greater than 70%, still more preferably greater than 90% by weight relative to the total weight of gel.

The method for obtaining insect eggs according to the invention is particularly suitable for breeding coleopterans and/or lepidopterans. The preferred coleopterans and/or lepidopterans are as indicated above, and more preferably the method for obtaining insect eggs according to the invention is particularly suitable for breeding *T. molitor*.

Other characteristics and advantages of the invention will become apparent from the following examples, given by way of illustration, with reference to the figures.

Example I: Preparation of an Egg-Laying Medium and a Laying Tray

The egg-laying medium is prepared using the following three components:
Solid substrate: white wheat feed, having a moisture content of 7%, the granulometry of which is as follows:
65% by weight of the particles have a size comprised between 0.30 and 0.50 mm,
30% by weight of the particles have a size smaller than 0.30 mm, and
5% by weight of the particles have a size comprised between 0.50 and 0.80 mm.
Gel: an aqueous gel is prepared from 98.7% by weight of water, 1% by weight of gelling agent (Flanogen) and 0.3% by weight of potassium sorbate.
FIG. 1 shows a laying tray 1.
The following is placed in a plastic container 2:
a solid substrate 3, namely 2000-4000 g white wheat feed (1-2 g/cm²);
an aqueous and optionally nutritional gel 4, namely 75-112.5 g aqueous gel (0.037-0.055 g/cm²).
Preferably, the components are introduced in the order indicated above.
A laying tray is thus obtained.

Example II: Method for Obtaining Insect Eggs

1. Material

Young *Tenebrio molitor* adults (aged 1 week)
Laying trays from Example I
A breeding room with controlled temperature and humidity A tumbler screening machine (Allgaier) or a linear screening machine (Mogensen)

2. Methods

Sorting of the adults; in order to populate the laying trays, a step of sorting based on mealworm beetles at the nymph stage may be necessary. With time, as the nymphs become adults, the adults are separated from the nymphs. The sorting of the nymphs from the adults is carried out over a period of time not exceeding 7 days. This sorting step thus makes it possible to obtain a homogeneous adult population (±7 days of difference in age within the population) in the laying tray.

Creation and population of the laying tray: the laying tray is created as indicated in Example I. The adults can originate from either the above sorting step or an old laying tray. In fact, the population of adults for the laying is kept for several weeks, for example 8 weeks, while the residences of the adults in a laying tray can last from 2 to 14 days. After that, at the end of a residence, the adults are sorted again, in particular in order to remove the dead adults and keep the living adults, then the latter are placed in a laying tray again in the optimum density of adults.

Adult mealworm beetles: 0.02-0.75 g/cm$^2$

Once the laying trays have been populated with adults, they are preserved in a breeding room having a relative humidity between 50% and 90%. It can be useful to re-supply the laying trays with aqueous gel. Typically, a quantity of aqueous gel (0.0074-0.275 g/cm$^2$) is supplied twice a week (i.e. an initial supply and a subsequent supply effected 3.5 days after the initial supply). The quantities of materials are calculated according to the surface area of the breeding tray.

Sorting/Collection of the eggs: the frequency of collection of the eggs can be adapted between 2 to 7 days. In the present example, the eggs were collected at the end of a 7-day period. On day 7, the laying tray is retrieved from the breeding room and its contents are poured into a screening machine. The screening machine has a set of sieves which makes it possible to separate, as a function of their size, the different fractions of the contents of the laying tray.

The step of sorting and collecting the eggs was tested with two different types of machine, a linear screening machine and a tumbler screening machine. The two machines gave good results during the collecting step.

Figure 2:
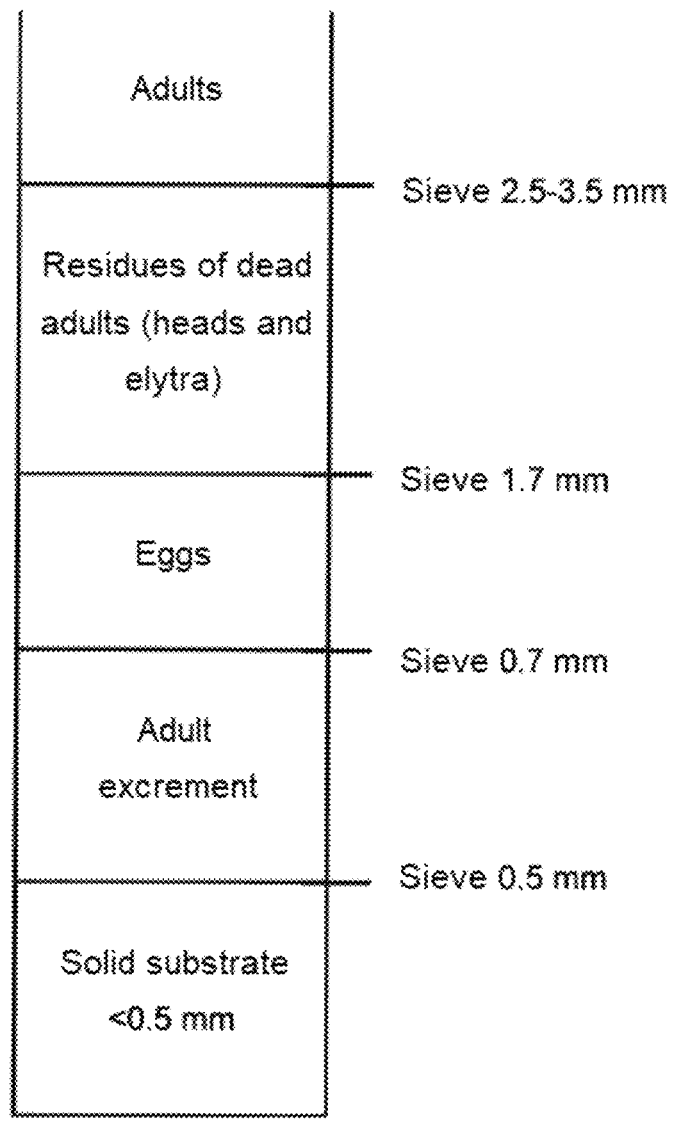
FIG. 2 is a diagram showing the separation of the different fractions during the automated step of sorting and collecting the insect eggs.

In FIG. 2, the separation of the different fractions as a function of their size is described:

Adult insect fraction: this fraction corresponds to the particles which do not pass through (or which are retained by) a sieve having an aperture size of at most 2.5 mm. This fraction contains living and dead adults. Over the course of one week of laying eggs in the solid substrate (wheat feed), a mortality of approximately 10% of the individuals was recorded. The living adults are then separated from the dead adults with the aid of a density separation. The living adults are deposited in the laying trays again.

Dead adult residue fraction: this fraction corresponds to the particles which pass through a sieve having an aperture size of at most 2.5 mm and are retained by a sieve having an aperture size of 1.7 mm. This fraction contains parts of dead adults (heads, legs, etc.).

Insect egg fraction: this fraction corresponds to the particles which pass through a sieve having an aperture size of 1.7 mm and are retained by a sieve having an aperture size of 0.7 mm. This fraction contains the eggs. The quantity of eggs obtained will depend on the conditions of the laying tray (density of the population, substrates, gel). Under the conditions of this example, an average of 25.9±5.68 eggs/cm$^2$ or 0.0186±0.0046 g eggs/cm$^2$ is obtained. The eggs obtained after the screening step are mixed with impurities: particles of solid substrate, some adult excrement and residues of dead adults. In fact, generally, after the sorting, the insect egg fraction still contains between 50 and 60% by weight of particles, excrement and residues (coarse waste).

Adult insect excrement fraction: this fraction corresponds to the particles which pass through a sieve having an aperture size of 0.7 mm and are retained by a sieve having an aperture size of 0.5 mm. This fraction contains the adult excrement.

Solid substrate fraction: this fraction corresponds to the particles which pass through a sieve having an aperture size of 0.5 mm. This solid substrate can then potentially be re-used.

Finally, when the supply of aqueous gel has been effected in the quantities indicated above, it is generally entirely consumed by the insects. If the aqueous gel has not been consumed, a sieve with a 5-mm mesh can be used in order to recover the pieces of dried gel.

Recovering the insect egg fraction makes it possible to collect the eggs. As indicated above, this fraction still between 50 and 60% by weight of particles, excrement and residues (coarse waste). After that, it can be used as is, or after an additional separation step in order to obtain a pure and clean egg fraction. In this case, the insect egg fraction is subjected to a density separation, such as a separation on a density column, with a rate of air-flow suitable for the quantity of eggs in order to make it possible to obtain pure and clean eggs. The pure and clean egg fraction then contains 65 to 75% by weight of eggs, a large part of the remaining 25 to 35% by weight being fine solid substrate particles.

In two egg fractions originating from a sorting of a laying tray the size of the solid substrate particles has not been selected in the first, while in the second, the egg fraction has been sorted according to the method according to the invention, the solid substrate having a granulometry suitable for sorting the eggs particles smaller than 0.5 mm, which leads to a higher-purity egg fraction.

Figure 3:
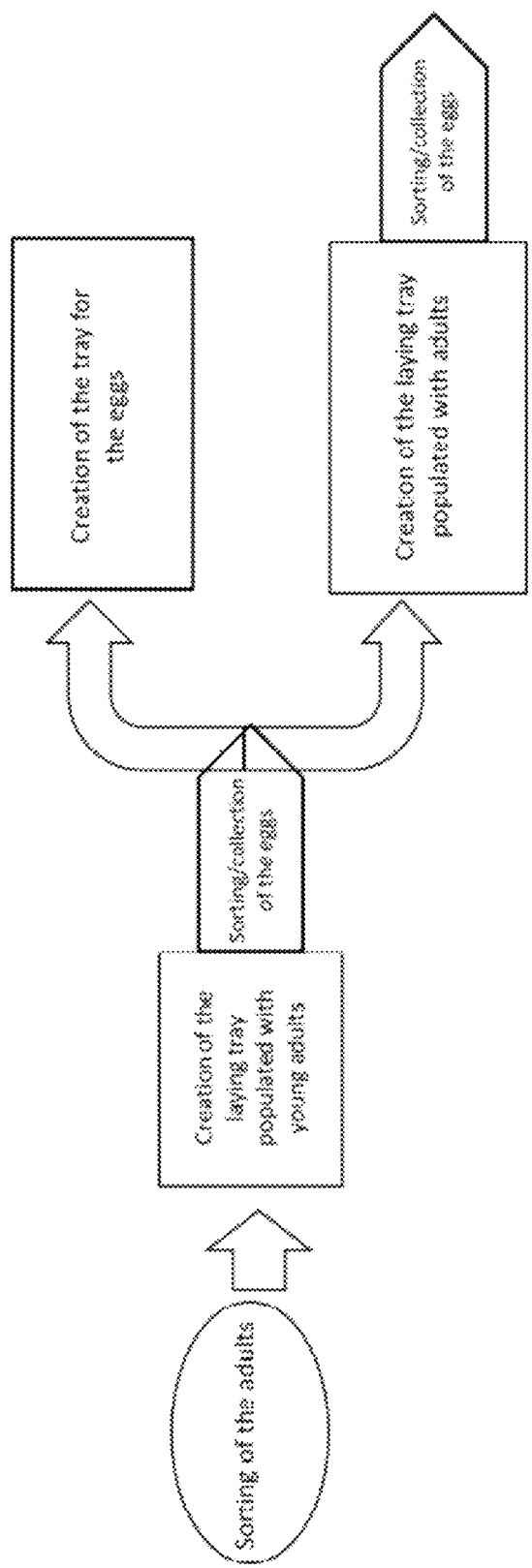
FIG. 3 is a diagram of "continuous" implementation of the method for obtaining insect eggs.

A diagram of "continuous" implementation of the method for obtaining insect eggs is shown in FIG. 3. This Figure is described in more detail below:

Sorting of the adults: see the above description of this step.

Laying tray populated with young adults: as indicated above, a laying tray is created then populated with young adults originating from the sorting of the adults.

Sorting/Collection of the eggs: see the above description of this step.

Creation of the tray for the eggs: this tray can then be populated with the egg fraction originating from the above collection, taking into account the fact that the mass of pure eggs is 55% in order to adapt the desired density of eggs, or with pure and clean eggs originating from the additional separation step. The eggs will hatch 6 to 10 days after creation of the tray for the eggs in order to give larvae.

Laying tray populated with adults: as indicated above, a laying tray is created then populated with adults recovered at the end of the step of sorting and collecting the eggs.

The invention claimed is:

1. Egg-laying medium for insects comprising:
   at least 80% by weight of a solid substrate or a mixture of solid substrates, in a form of particles, at least 85% by weight of said particles having a particle size smaller than 0.5 mm, wherein said solid substrate or mixture of solid substrates is a solid product or co-product originating from a conversion of cereals, oilseeds, protein-oil crops and/or protein crops and has a moisture content comprised between 0 and 15% the solid substrate, and at least 2% by weight of an aqueous gel, wherein the percentages by weight are given in relation to a total weight of said egg-laying medium for insects.

2. The egg-laying medium for insects according to claim 1, wherein the aqueous gel comprises:

at least 90% by weight of an aqueous solution,
0.3 to 2% by weight of a gelling agent, and
0.1 to 5% by weight of a preservative, wherein the percentages by weight are expressed in relation to a total weight of said gel.

3. The egg-laying medium for insects according to claim 1, wherein the aqueous gel has a gel strength of at least 20 g/cm².

4. Laying tray comprising a container with a bottom and, on said bottom of said container, an egg-laying medium according to claim 1.

5. The egg-laying medium for insects according to claim 1, wherein the aqueous gel comprises a liquid agro-industrial coproduct, yeasts, vitamins, and/or probiotics.

6. A method for breeding coleopterans and/or lepidopterans comprising using the egg-laying medium for insects according to claim 1.

7. Laying tray comprising a container with a bottom and, on said bottom of said container:

0.12 to 7.5 g/cm² of a solid substrate or a mixture of solid substrates in a form of particles, at least 85% by weight of said particles having a particle size smaller than 0.5 mm, wherein said solid substrate or mixture of solid substrates is a solid product or co-product originating from a conversion of cereals, oilseeds, protein-oil crops and/or protein crops and has a moisture content comprised between 0 and 15%.

8. Laying tray according to claim 7, further comprising, on said bottom of said container:

0.006 to 0.325 g/cm² or 0.0016 to 0.095 g/cm²/d of an aqueous gel.

9. Laying tray according to claim 8, wherein the aqueous gel comprises a liquid agro-industrial coproduct, yeasts, vitamins, and/or probiotics.

10. A method for obtaining insect eggs, comprising steps of:

obtaining a laying tray by providing a container and filling said container with:

a solid substrate or a mixture of solid substrates in a form of particles, at least 85% by weight of said particles having a particle size smaller than 0.5 mm, wherein said solid substrate or mixture of solid substrates is a solid product or co-product originating from a conversion of cereals, oilseeds, protein-oil crops and/or protein crops and has a moisture content comprised between 0 and 15%, introducing adult insects into the laying tray, and
a subsequent step of collecting the insect eggs.

11. The method for obtaining insect eggs according to claim 10, wherein the step of filling the container with the solid substrate is effected by supplying 0.12 to 7.5 g/cm² of said solid substrate into the container.

12. The method for obtaining insect eggs according to claim 10, wherein the step of obtaining a laying tray further comprises filling said container with:

0.0016 to 0.095 g/cm²/d of an aqueous gel.

13. The method for obtaining insect eggs according to claim 12, wherein the aqueous gel comprises a liquid agro-industrial coproduct, yeasts, vitamins, and/or probiotics.

14. The method for obtaining insect eggs according to claim 10, wherein the step of introducing the adult insects is effected in an areal density in the laying tray comprised between 0.01 and 1.0 g/cm².

15. The method for obtaining insect eggs according to claim 10, wherein the subsequent step of collecting the eggs is effected by an automated sorter.

16. The method for obtaining insect eggs according to claim 15, wherein said automated sorter is a tumbler screening machine or a linear screening machine.

17. The method for obtaining insect eggs according to claim 10, wherein the adult insects are coleopterans and/or lepidopterans.

* * * * *